US009861493B2

(12) United States Patent
Maale

(10) Patent No.: US 9,861,493 B2
(45) Date of Patent: Jan. 9, 2018

(54) GLENOID FOSSA PROSTHESIS

(71) Applicant: Gerhard E. Maale, Plano, TX (US)

(72) Inventor: Gerhard E. Maale, Plano, TX (US)

( * ) Notice: Subject to any disclaimer, the term of this patent is extended or adjusted under 35 U.S.C. 154(b) by 89 days.

(21) Appl. No.: 14/827,167

(22) Filed: Aug. 14, 2015

(65) Prior Publication Data

US 2017/0042688 A1 Feb. 16, 2017

(51) Int. Cl.
*A61F 2/40* (2006.01)
*A61F 2/30* (2006.01)

(52) U.S. Cl.
CPC ........ *A61F 2/4081* (2013.01); *A61F 2/30907* (2013.01); *A61F 2002/3092* (2013.01); *A61F 2002/3093* (2013.01); *A61F 2002/30242* (2013.01); *A61F 2002/30332* (2013.01); *A61F 2002/30433* (2013.01); *A61F 2002/30772* (2013.01); *A61F 2002/30774* (2013.01); *A61F 2002/30878* (2013.01); *A61F 2002/4085* (2013.01)

(58) Field of Classification Search
CPC .. A61F 2/40; A61F 2/4081; A61F 2/34; A61F 2002/4085; A61F 2002/4088; A61F 2002/4092
See application file for complete search history.

(56) References Cited

U.S. PATENT DOCUMENTS

| 4,776,851 | A | 10/1988 | Bruchman et al. |
|---|---|---|---|
| 5,489,309 | A | 2/1996 | Lackey et al. |
| 5,549,687 | A | 8/1996 | Coates et al. |
| 6,214,049 | B1 | 4/2001 | Gayer et al. |
| 6,663,670 | B2 | 12/2003 | Rogers et al. |
| 6,676,704 | B1 * | 1/2004 | Pope .................. A61F 2/30767 623/18.11 |
| 7,175,664 | B1 | 2/2007 | Lakin |
| 7,297,163 | B2 | 11/2007 | Huebner |
| 7,435,263 | B2 | 10/2008 | Barnett et al. |
| 8,292,895 | B2 | 10/2012 | Bubb |

(Continued)

FOREIGN PATENT DOCUMENTS

| DE | 19931670 C1 | 2/2001 |
|---|---|---|
| FR | 2776506 A1 | 1/1999 |
| WO | 2005087142 A2 | 9/2005 |
| WO | 2012051552 A2 | 4/2012 |

OTHER PUBLICATIONS

International Searching Authority; International Search Report; PCT/US2015/51036; dated Dec. 17, 2015.

(Continued)

*Primary Examiner* — Brian Dukert
(74) *Attorney, Agent, or Firm* — Steven H. Washam; Washam PLLC

(57) ABSTRACT

An endoprosthetic device for replacement of a diseased or damaged scapular glenoid fossa. The device includes a glenosphere or a glenosocket member, or provides the option of mating a glenosphere or glenosocket member via a Morse taper. The device also features opposing fixation plates that grip resected scapular area anteroposteriorly to fixate the device through use of a plurality of setscrews. An Oblique setscrew that engages the scapular body inferiorly may be added for improved fixation. A porous mesh surface treatment on the inner faces of the fixation plates may be utilized to improve osteoconductivity.

15 Claims, 4 Drawing Sheets

(56) References Cited

U.S. PATENT DOCUMENTS

| | | |
|---|---|---|
| 8,343,226 B2 | 1/2013 | Nogarin et al. |
| 8,986,398 B2 | 3/2015 | Poulson et al. |
| 2009/0319055 A1 | 12/2009 | Iversen et al. |
| 2013/0090695 A1 | 4/2013 | Bernstein et al. |
| 2013/0090737 A1* | 4/2013 | Flaherty ............... A61F 2/40 623/19.13 |
| 2013/0123929 A1 | 5/2013 | McDaniel et al. |
| 2014/0025173 A1* | 1/2014 | Cardon .............. A61F 2/4081 623/19.13 |

OTHER PUBLICATIONS

International Searching Authority; Written Opinion; PCT/US2015/51036; dated Dec. 17, 2015.
Derwent Abstract of DE 199 31 670 C1 Reference to Grundei, et al. (Jul. 8, 1999); Thomson Reuters; 2016.
R. Newsham-West, H. Nicholson, M. Walton, and P. Milburn; Long-term morphology of a healing bone-tendon interface: a histological observation in the sheep model; Journal of Anatomy; 2007; pp. 318-327; vol. 210; Anatomical Society of Great Britain and Ireland; Blackwell Publishing Ltd.; John Wiley & Sons; USA.
Robert Henshaw and Martin Malawer; Review of Endoprosthetic Reconstruction in Limb-sparing Surgery; Musculoskeletal Cancer Surgery Treatment of Sarcomas and Allied Diseases; 2001; pp. 381-402; Kluwer Academic Publishers; USA.
Zimmer; Anatomical Shoulder System; Zimmer Inc.; www.zimmer.com; 2010; USA.

* cited by examiner

GLENOID FOSSA PROSTHESIS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to endoprosthetic devices and, more specifically, to a scapular endoprosthetic device for full repair of glenoid defects.

Description of Related Art Including Information Disclosed Under 37 CFR 1.97 and 1.98

Patients suffering from diseases or deformities of the glenoid fossa of the scapula, prior to the instant invention, have very few options for repair. Bone grafts are sometimes utilized, relying on healthy bone (if available) from another area of the patient's body, donated bone from a cadaver, or synthetic bone in certain situations. However, such real bone grafts are limited in usefulness due to the complexities of the shoulder joint, and are problematic with regard to patient reactions to medication, bleeding, post-operative infection, and attendant pain at the harvest and graft sites. Synthetic bone, on the other hand, while reducing the incidence of rejection and post-operative infection, is limited in usefulness as well due to, again, the complexities of the shoulder joint and the physical stresses experienced therein during normal joint operation.

Current glenohumeral repair techniques include hemiarthroplasty (resurfacing or stemmed), total shoulder replacement, or reverse total shoulder replacement. Resurfacing hemiarthroplasty involves resurfacing of the humeral head joint surface with a cap-like prosthesis of highly polished metal. This is a relatively minimal repair, that relies on the existence of adequate cartilage within the glenoid fossa and a generally otherwise healthy humerus. A stemmed hemiarthroplasty involves a prosthetic humeral head joint surface with an intramedullary stem for fixation within the humeral shaft. This type of repair is often necessitated by severe fractures of the humeral head, but requires a relatively healthy glenoid with intact cartilage surface.

Total shoulder replacement, as the name implies, involves replacement of the entire glenohumeral joint and is typically necessitated by severe arthritis, physical damage, or disease action resulting in loss of joint cartilage. In a standard total shoulder replacement a stemmed hemiarthroplasty repair is mated with a glenoid socket prosthetic component to complete the artificial shoulder joint. The glenoid socket component is either cemented or "press-fit" into the bone of the original glenoid fossa. In a reverse total shoulder replacement scenario the socket and ball components of the repair are reversed, such that the socket portion is fixated on the humeral head and the metal ball portion is fixated in the glenoid fossa.

The current repair methods—hemiarthroplasty and total shoulder repair—each require adequate scapular structure for support and fixation. In instances where disease process has deteriorated the scapular structure such that the glenoid fossa and surrounding bone is not viable, existing repair devices and techniques are useless. What is needed is a scapular glenoid fossa replacement device to effect shoulder repair to restore patient function in such instances of scapular deficiency.

BRIEF SUMMARY OF THE INVENTION

The present invention is embodied in numerous forms, including an embodiment of a glenoid fossa endoprosthetic device, the device comprising: a glenosphere or glenosocket joint component including a first and second fixation plate affixed thereto, the first and second fixation plates disposed to form a space therebetween for receiving a scapula neck of a patient, the first fixation plate having a plurality of holes for placement of setscrews, the threads of which to be received by the second fixation plate. In another embodiment the device further comprises an oblique setscrew for fixation of the device to the inferior body of the scapula neck. In yet another embodiment the device, wherein the second fixation plate comprises a plurality of setscrew holes that correspond with the first fixation plate setscrew holes, the device further comprises a thread engagement plate for attachment to the first or second fixation plate, the attached thread engagement plate for receiving the threads of a setscrew placed in the hole of the other fixation plate. In yet another embodiment the device further comprises a porous mesh surface treatment on an inner surface of a fixation plate to improve osteoconductivity.

The present invention includes another embodiment of a glenoid fossa endoprosthetic device comprising: a Morse taper and a first and second fixation plate affixed thereto, the first and second fixation plates forming a space therebetween for receiving a scapula neck of a patient, the first fixation plate having a plurality of holes for placement of setscrews, the threads of which to be received by the second fixation plate, the Morse taper for receiving a glenosphere or glenosocket joint component. In yet another embodiment the device further comprises a glenosphere or glenosocket joint component. In yet another embodiment the device further comprises an oblique setscrew for fixation of the device to the inferior body of the scapula neck. In yet another embodiment the device, wherein the second fixation plate comprises a plurality of setscrew holes that correspond with the first fixation plate setscrew holes, the device further comprises a thread engagement plate for attachment to the first or second fixation plate, the attached thread engagement plate for receiving the threads of a setscrew placed in the hole of the other fixation plate. In yet another embodiment the device further comprises a porous mesh surface treatment on an inner surface of a fixation plate to improve osteoconductivity.

The present invention is also embodied in a glenoid fossa repair method, the method steps comprising: resecting all or a portion of a glenoid fossa of a scapula of a patient to remove diseased or damaged tissue; selecting a glenosphere or glenosocket joint component, the component comprising a first and second fixation plate affixed thereto, the first and second fixation plates disposed to form a space therebetween for receiving a scapula neck of a patient, the first fixation plate having a plurality of holes for placement of setscrews, the threads of which to be received by the second fixation plate; positioning the first and second fixation plates over the scapular resection to position the glenosphere or glenosocket joint component in the approximate position of the resected glenoid fossa; fixating the first and second fixation plates to the scapula by passing a setscrew through each of the first fixation plate setscrew holes and corresponding holes formed in the scapula neck of the patient to engage the corresponding hole in the second fixation plate, wherein the setscrew threads grip the second fixation plate to compress the scapula neck between the first and second fixation plates; and completing the shoulder joint repair. Steps of additional embodiments further comprise: installing an oblique setscrew through the lateral end of the glenosphere or glenosocket joint component for fixation of the joint component to the inferior body of the scapula neck. In another embodiment, wherein the second fixation plate comprises a plurality of setscrew holes that correspond with the first fixation plate setscrew holes, the method steps further comprise: installing a thread engagement plate on the second fixation plate, the attached thread engagement plate for receiving the threads of a setscrew placed in the hole of the first fixation plate. Another embodiment, wherein the joint component further comprises a Morse taper, the method steps further comprise: selecting a glenosphere head or a glenosocket head for the shoulder repair and installing the selected head on the Morse taper. In another embodiment, wherein the joint component further comprises a Morse taper, the method steps further comprise: installing an oblique setscrew through the Morse taper for fixation of the joint component to the inferior body of the scapula neck; and selecting and installing on the Morse taper a glenosphere head or a glenosocket head for the shoulder repair.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein.

Figure 1:
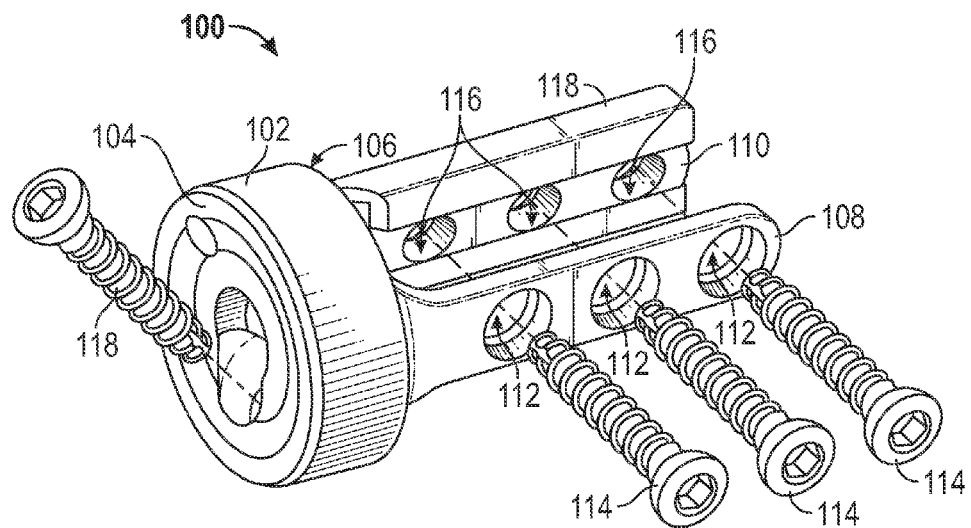
FIG. 1 is a depiction of an embodiment of the glenoid fossa endoprosthetic device invention featuring a glenosocket joint component.

The above figures are provided for the purpose of illustration and description only, and are not intended to define the limits of the disclosed invention. Use of the same reference number in multiple figures is intended to designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

FIG. 1 is a depiction of an embodiment of the glenoid fossa endoprosthetic device invention featuring a glenosocket joint component (100). As shown, the glenosocket member (102) has a lateral face (104) with which to engage the complimentary humeral head feature on a patient's humerus, and a medial face (106) having a first fixation plate (108) and a second fixation plate (110) extending therefrom. The fixation plates are substantially rigid, and are either formed as part of the medial face during the machining process, or otherwise attached using a common metal bonding process. The machined members and all other metal components of the embodiment are manufactured from biologically compatible and stable metals. In the instant embodiment the glenosocket joint components are titanium, but may be surgical stainless steel, niobium, gold, platinum, or the like, or some combination thereof. Moreover, combinations of metals and/or biocompatible polymers may also be utilized and are within the scope of the claimed invention.

The fixation plates (108 and 110) are substantially parallel and are positioned to form a space therebetween for receiving the resected scapula neck area of the scapula of a patient. The anteroposterior thickness of the scapula in this area varies among patients, with an adult patient measuring approximately 15 mm to 22 mm and a child patient approximately 10 mm to 15 mm. However, the thickness and composition of the fixation plates (108 and 110) is such that a minimal amount of flexure is accommodated to allow for superior gripping of the resected scapula area during fixation. The device is easily sized in this regard in order to accommodate any patient.

The first fixation plate (108) features a plurality of holes (112) to allow placement and passage of fixation setscrews (114). In the instant invention the setscrews (114) are hex headed countersunk screws that utilize a countersunk hole to maintain the head of the screw substantially flush with the fixation plate upon installation. Further, the thread tip is tapered and features a cutting edge feature for cutting threads in metal upon rotation. A plurality of corresponding holes (116) in the second fixation plate (110) receives the threaded portion of the setscrews and allows threads to be cut therein. Accordingly, upon device installation, the gap between the first and second fixation plates decreases as the setscrews draw the fixation plates inward with setscrew (114) rotation. Though a particular setscrew is depicted and described, one of ordinary skill will appreciate that other common setscrews may also be utilized.

In another embodiment the glenoid fossa endoprosthetic device also utilizes a thread engagement plate (118) for gripping of the threaded portion of the setscrews (114). As depicted the thread engagement plate (118) is formed to provide a channel to receive the first or second fixation plate (108 and 110). In this configuration the setscrew holes in each fixation plate are of the same diameter to allow the setscrews to be placed from either direction. For example, if the surgeon chooses to place the setscrews through the first fixation plate (108) and into the second fixation plate (110), the thread engagement plate (118) is added to the second fixation plate (110) as shown so that the setscrew (114) thread tip may cut threads into the thread engagement plate (118) holes.

It is also possible to splay the setscrews (114), or otherwise allow one or more of the setscrews to enter a hole at an oblique angle. The device also allows the use of an oblique setscrew (118) that enters from the glenosocket face (104) on an oblique angle in order to engage the remaining scapula body inferiorly to provide added fixation and stability to the repair.

Figure 2:
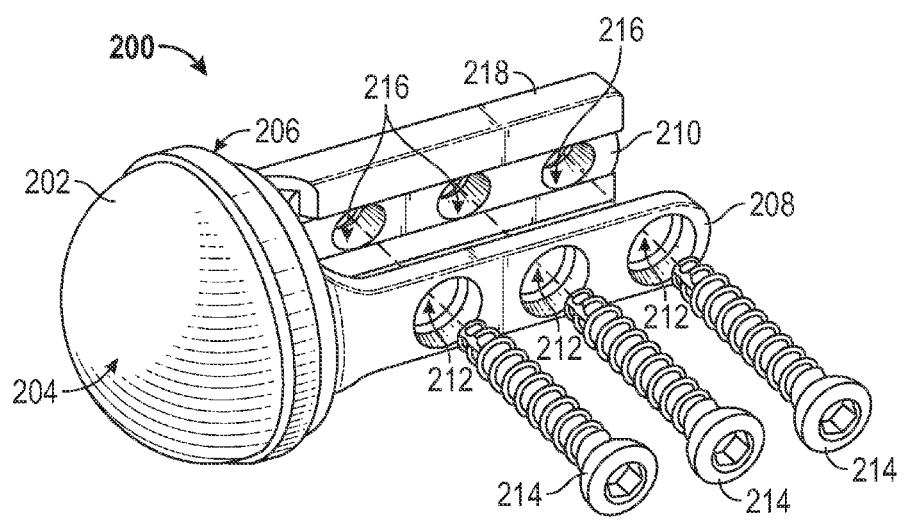
FIG. 2 is a depiction of another embodiment of the glenoid fossa endoprosthetic device invention featuring a glenosphere joint component.

FIG. 2 is a depiction of another embodiment of the glenoid fossa endoprosthetic device invention featuring a glenosphere joint component (200). As shown, the glenosphere member (202) has a lateral face (204) with which to engage the complimentary humeral head feature on a patient's humerus (in this instance, in a reverse total shoulder arrangement), and a medial face (206) having a first fixation plate (208) and a second fixation plate (210) extending therefrom. Other than the glenosphere member (202), this embodiment shares features and functionality with the previous embodiment. Each fixation plate (208 and 210) features a plurality of holes (212 and 216) for placement of setscrews (214) therethrough. Threads from the setscrews (214) may engage the fixation plate (210) material, or an optional thread engagement plate (218).

Figure 3:
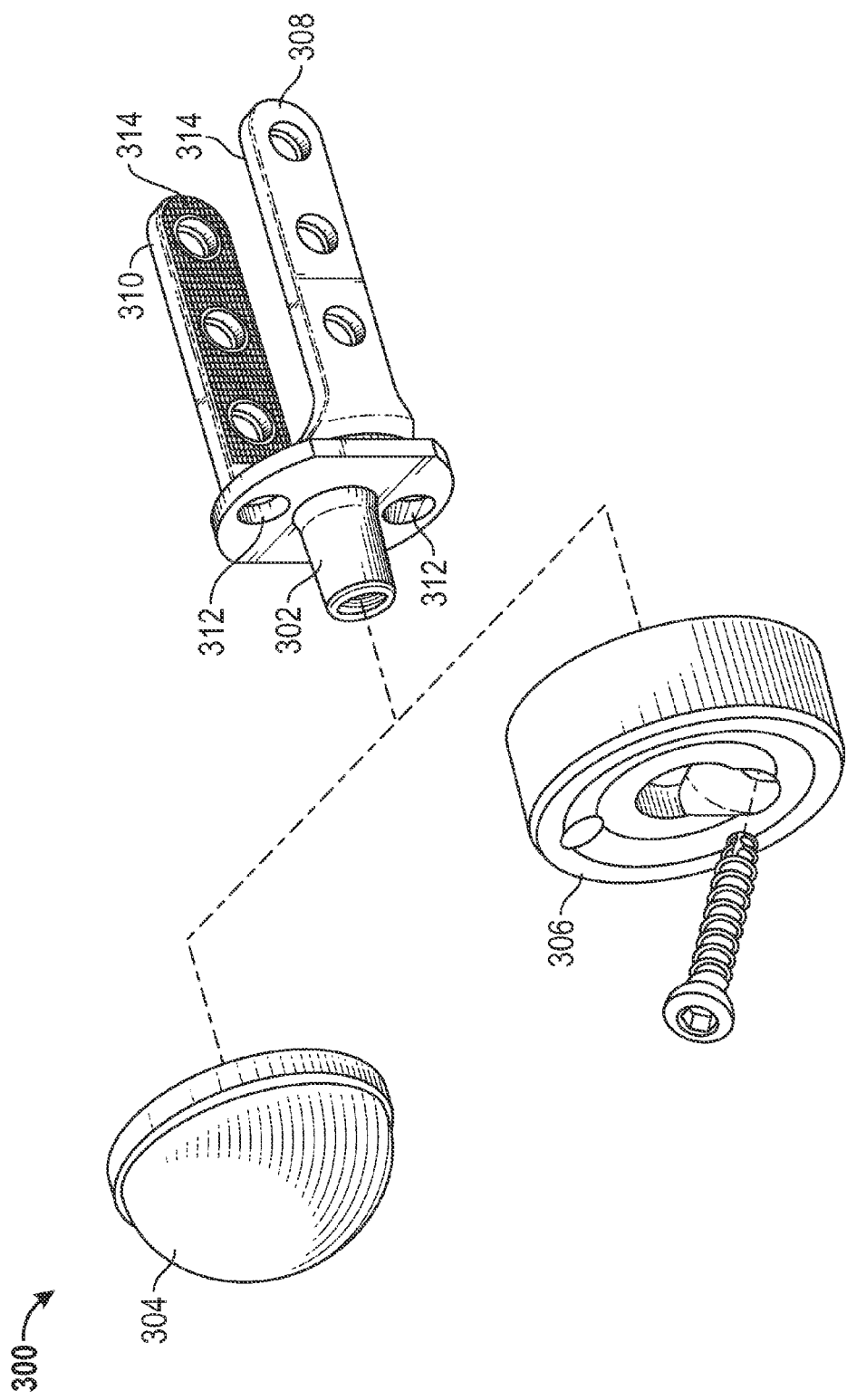
FIG. 3 is a depiction of another embodiment of the glenoid fossa endoprosthetic device invention featuring a Morse taper device allowing for interchangeable glenosphere and glenosocket members.

FIG. 3 is a depiction of another embodiment of the glenoid fossa endoprosthetic device invention featuring a Morse taper device allowing for interchangeable glenosphere and glenosocket members (300). As shown, the device utilizes a Morse taper member (302) for accepting either a glenosphere member (304) or a glenosocket member (306). The benefit to this configuration is that a single shoulder joint repair kit may include the option of a standard or reverse total shoulder configuration. The device configuration may be determined prior to installation, and the appropriate glenosocket/glenosphere member may be subsequently installed.

The medial face, as with the previous embodiments, has a first fixation plate (308) and a second fixation plate (310) extending therefrom. Setscrews utilize the holes therethrough for affixation of the device to the resected scapula as before. Additional oblique setscrews may be utilized (312) for added stability. A porous mesh surface treatment is also applied to the inner surfaces (314) of the fixation plates (308 and 310) to improve osteoconductivity. This porous mesh surface treatment may be utilized in the previous embodiments and has the added benefit of providing for greater stability of the overall repair.

Figure 4:
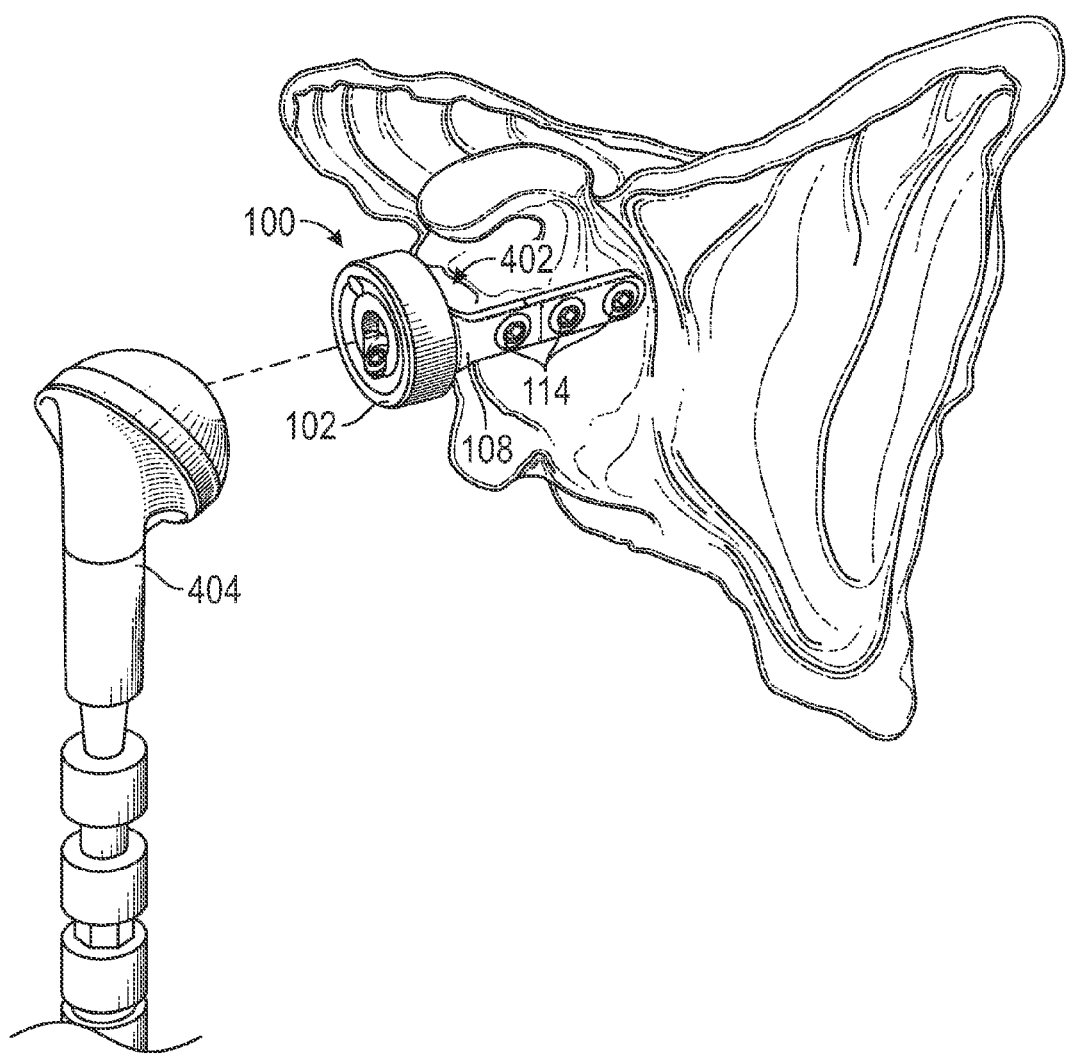
FIG. 4 is a depiction of the glenoid fossa endoprosthetic device invention as installed in a standard total shoulder repair arrangement.

FIG. 4 is a depiction of the glenoid fossa endoprosthetic device invention as installed in a standard total shoulder repair arrangement. As shown, an embodiment of the glenosocket joint component (100) is chosen, but the Morse taper embodiment with a glenosocket feature may also be utilized. One of ordinary skill will appreciate that the repair relies on common surgical procedures for performing a standard total shoulder joint repair.

The patient's glenoid fossa/scapula neck (402) area is exposed and the diseased or injured tissue is removed to achieve a clean margin. The remaining bone is prepared, with sufficient bone removed to prevent impingement with the repair device (100). The repair device first and second fixation plates (108 and 110) are positioned over the scapular resection to position the glenosocket joint component in the approximate location of the original glenoid fossa. The device is thin fixated by installing the setscrews (114) through the first fixation plate (108) into the second fixation plate (110—not shown). The setscrews (114) may engage the second fixation plate directly, or may engage an added thread engagement plate as described above. As the setscrews (114) are tightened the fixation plates (108 and 110) compress slightly to further grip the scapula. An optional oblique setscrew (118) may also be utilized to engage the remaining scapula neck inferiorly. The shoulder joint repair may then be completed as with a standard total shoulder repair by joining the glenosocket (102) with the humeral head component (404).

Figure 5:
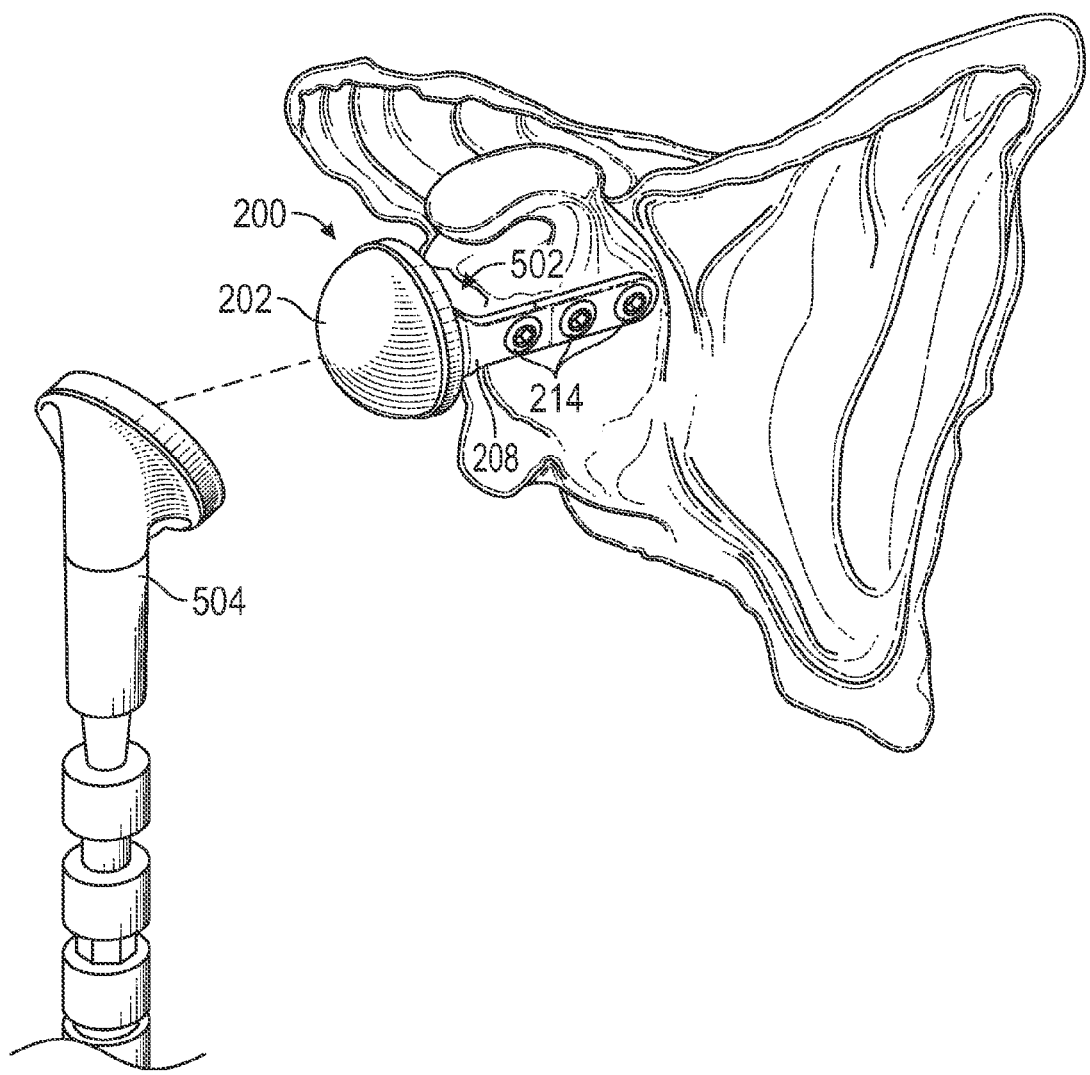
FIG. 5 is a depiction of the glenoid fossa endoprosthetic device invention as installed in a reverse total shoulder repair arrangement.

FIG. 5 is a depiction of the glenoid fossa endoprosthetic device invention as installed in a reverse total shoulder repair arrangement. As shown, an embodiment of the glenosphere joint component (200) is chosen, but the Morse taper embodiment with a glenosphere feature may also be utilized. One of ordinary skill will appreciate that this repair, likewise, relies on common surgical procedures for performing a reverse total shoulder joint repair.

As above, the patient's glenoid fossa/scapula neck (502) area is exposed and the diseased or injured tissue is removed to achieve a clean margin. The remaining bone is prepared, with sufficient bone removed to prevent notching with the repair device (100). The repair device first and second fixation plates (208 and 210) are positioned over the scapular resection to position the glenosocket joint component in the approximate location of the original glenoid fossa. The device is thin fixated by installing the setscrews (214) through the first fixation plate (208) into the second fixation plate (210—not shown). The setscrews (214) may engage the second fixation plate directly, or may engage an added thread engagement plate as described above. As the setscrews (214) are tightened the fixation plates (208 and 210) compress slightly to further grip the scapula. The shoulder joint repair may then be completed as with a standard total shoulder repair by joining the glenosphere (202) with the complimentary humeral head component (504).

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are to be embraced by the claims. Further, the recitation of method steps does not denote a particular sequence for execution of the steps. Such method steps may therefore be performed in a sequence other than that recited unless the particular claim expressly states otherwise.

I claim:

1. A glenoid fossa endoprosthetic device, the device comprising:

a glenosphere or glenosocket joint component for a scapular deficient patient, including a first and second fixation plate affixed thereto, the first and second fixation plates forming a space therebetween for receiving only a scapula neck of the scapular deficient patient, the first fixation plate having a plurality of holes for placement of a setscrew therein and the second fixation plate having a plurality of holes corresponding to the first fixation plate holes for receiving the setscrew threads; and a thread engagement plate having a length-wise channel formed therein, the channel for receiving the first or second fixation plate for attachment thereto, the thread engagement plate including a plurality of holes corresponding to the first or second fixation plate holes.

2. The glenoid fossa endoprosthetic device of claim 1, wherein the second fixation plate holes are sized to engage the setscrew threads to allow the formation of threads within the engaged hole.

3. The thread engagement plate of claim 1,
wherein the plurality of holes are sized to engage the threads of the setscrew to allow the formation of threads within the engaged hole.

4. The glenoid fossa endoprosthetic device of claim 1, the device further comprising:
a porous mesh surface treatment on an inner surface of a fixation plate to improve osteoconductivity.

5. A glenoid fossa endoprosthetic device, the device comprising:
a Morse taper and a first and second fixation plate affixed thereto, the first and second fixation plates forming a space therebetween for receiving only a scapula neck of a scapular deficient patient, the first fixation plate having a plurality of holes for placement of a setscrew therein and the second fixation plate having a plurality of holes corresponding to the first fixation plate holes for receiving the setscrew threads, the Morse taper for receiving a glenosphere or glenosocket joint component; and
a thread engagement plate having a length-wise channel formed therein, the channel for receiving the first or second fixation plate for attachment thereto, the thread engagement plate including a plurality of holes corresponding to the first or second fixation plate holes.

6. The glenoid fossa endoprosthetic device of claim 5, the device further comprising:
a glenosphere or glenosocket joint component.

7. The glenoid fossa endoprosthetic device of claim 5, wherein the second fixation plate holes are sized to engage the setscrew threads to allow the formation of threads within the engaged hole.

8. The thread engagement plate of claim 5,
wherein the plurality of holes are sized to engage the threads of the setscrew to allow the formation of threads within the engaged hole.

9. The glenoid fossa endoprosthetic device of claim 5, the device further comprising:
a porous mesh surface treatment on an inner surface of a fixation plate to improve osteoconductivity.

10. A glenoid fossa repair method, the method steps comprising:
in a scapular deficient patient, selecting a glenosphere or glenosocket joint component, the component comprising a first and second fixation plate affixed thereto, the first and second fixation plates forming a space therebetween for receiving only a scapula neck of the scapular deficient patient, the first fixation plate having a plurality of holes for placement of a setscrew therein and the second fixation plate having a plurality of holes corresponding to the first fixation plate holes for receiving the setscrew threads;
positioning the first and second fixation plates over the scapular resection to position the glenosphere or glenosocket joint component in the approximate position of the resected glenoid; and
fixating the first and second fixation plates to the scapula by passing a setscrew through each of the first fixation plate setscrew holes and corresponding holes formed in the scapula neck of the patient to engage the corresponding hole in the second fixation plate, wherein the setscrew threads engage the second fixation plate.

11. The glenoid fossa repair method of claim 10, the method steps further comprising:
installing an oblique setscrew through the lateral end of the glenosphere or glenosocket joint component for fixation of the joint component to the inferior body of the scapula neck.

12. The glenoid fossa repair method of claim 10, the method steps further comprising:
installing a thread engagement plate onto the first or second fixation plate, the attached thread engagement plate including a plurality of holes corresponding to the attached fixation plate holes, the plurality of holes sized to engage the threads of the setscrew, wherein the setscrew threads form threads within the engagement plate hole.

13. The glenoid fossa repair method of claim 10, wherein the joint component further comprises a Morse taper, the method steps further comprising:
selecting a glenosphere head or a glenosocket head for the shoulder repair and installing the selected head on the Morse taper.

14. The glenoid fossa repair method of claim 10, wherein the joint component further comprises a Morse taper, the method steps further comprising:
installing an oblique setscrew through the Morse taper for fixation of the joint component to the inferior body of the scapula neck; and
selecting and installing on the Morse taper a glenosphere head or a glenosocket head for the shoulder repair.

15. The glenoid fossa repair method of claim 10, the method steps further comprising:
creating a scapular deficient patient by resecting a glenoid of a scapula of a patient to remove diseased or damaged tissue.

* * * * *